United States Patent [19]

Norman et al.

[11] Patent Number: 4,735,634
[45] Date of Patent: Apr. 5, 1988

[54] PILLARED COBALT COMPLEXES FOR OXYGEN SEPARATION

[75] Inventors: John A. T. Norman, Whitehall; Dorai Ramprasad, Allentown, both of Pa.; Daryle H. Busch, Columbus, Ohio

[73] Assignee: Air Products and Chemicals, Inc., Allentown, Pa.

[21] Appl. No.: 901,481

[22] Filed: Aug. 28, 1986

[51] Int. Cl.[4] .................. B01D 53/22; B01D 53/14
[52] U.S. Cl. .................................. 55/16; 55/68; 55/158; 423/219
[58] Field of Search .................. 55/16, 68, 158; 423/219, 579

[56] References Cited

U.S. PATENT DOCUMENTS

| | | | |
|---|---|---|---|
| 2,450,276 | 9/1948 | Fogler et al. | 423/579 |
| 2,523,549 | 9/1950 | Axe | 423/219 X |
| 3,396,510 | 8/1968 | Ward, III et al. | 55/16 |
| 4,011,306 | 3/1977 | Fox, Jr. | 423/579 |
| 4,032,617 | 6/1977 | Gay | 423/219 |
| 4,343,715 | 8/1982 | Bonaventura et al. | 55/68 X |
| 4,421,530 | 12/1983 | Dalton, Jr. et al. | 55/62 X |
| 4,421,531 | 12/1983 | Dalton, Jr. et al. | 55/62 X |
| 4,427,416 | 1/1984 | Bonaventura et al. | 55/68 X |
| 4,451,270 | 5/1984 | Roman | 55/38 |
| 4,542,010 | 9/1985 | Roman | 423/579 |
| 4,584,359 | 4/1986 | Sterzel et al. | 526/241 |
| 4,602,987 | 7/1986 | Bonaventura et al. | 423/579 X |
| 4,605,475 | 8/1986 | Roberts et al. | 55/68 X |

OTHER PUBLICATIONS

D. H. Busch et al., "Molecular Species Containing Persistent Voids, Template Synthesis and Characterization of a Series of Lacunar-Nickel (II) Complexes and the Corresponding Free Ligands", J. Am. Chem. Soc., 1981, 103, pp. 1472-1478.
K. Kasuga et al., "The Preparation and Some Properties of Cobalt (II) Schiff Base Complexes and Their Molecular Oxygen Adducts", Bull. Chem. Soc. Jpn, 56, 95-98, (1983).
P. J. McCarthy et al., "Inner Complex Chelates, I. Analogs of Bisacetylacetoneethylene-Diimine and its Methal Chelates", J. Am. Chem. Soc., 1955, vol. 077, pp. 5820–5824.

Francis C. Ray, et al., "Diels–Alder Reactions of Malemide", JACS, 74, pp. 1247-1248, (1952).
Y. Y. Chen et al., "High-Spin Five-Coordinate Complexes of Cobalt (II), Nickel (II), and Copper (II) with Linear, Pentadantate Keta Iminata Ligands", Inorg. Chem., 1981, 20, 1885-1892.

*Primary Examiner*—Robert Spitzer
*Attorney, Agent, or Firm*—Mark L. Rodgers; William F. Marsh; James C. Simmons

[57] ABSTRACT

The present invention is a cobalt complex having the structural formula:

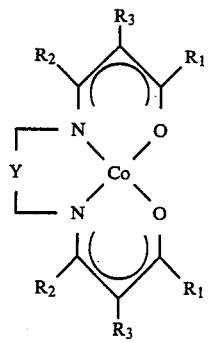

wherein each $R_1$ is independently, a phenyl or a $C_1$-$C_6$ alkyl group; each $R_2$ is independently hydrogen, a phenyl, or a $C_1$-$C_6$ alkyl group; $R_3$ is either N-succinimido substituted with a $C_3$ or greater hydrocarbon functionality at the carbon atoms $\alpha$ to the imido carbonyl carbons, or a carbonyl functionality having a $C_1$ greater hydrocarbon substituent with the proviso that if said substituent is methyl, $R_2$ cannot be hydrogen; and Y is o-phenylene, $-CH_2-_a$, wherein "a" is 2 or 3, $-CH_2-_b NR_4-CH_2-_c$, wherein "b" and "c" are independently 2 or 3 and $R_4$ is hydrogen or a $C_1$-$C_{12}$ alkyl group.

These complexes have the ability to selectively and reversibly bind oxygen, thus making them useful components of oxygen separation membranes and absorbents.

20 Claims, No Drawings

PILLARED COBALT COMPLEXES FOR OXYGEN SEPARATION

TECHNICAL FIELD OF THE INVENTION

The present invention relates to metal complexes that reversibly react with molecular oxygen and are suitable for use in air separation processes.

BACKGROUND OF THE INVENTION

Oxygen is produced industrially in enormous quantities from air. Currently, a majority of industrially-produced oxygen is separated from air by condensing the air and then fractionally distilling the liquid air to separate the oxygen from nitrogen and other gases. This liquefaction procedure consumes very large amounts of energy, since the boiling point of oxygen at atmospheric pressure is only 77° K.

In view of the known disadvantages of the air liquefaction process, attention has recently been directed toward methods for the separation of oxygen from air at temperatures much closer to ambient. In principle, such separation methods are very simple; a solution is prepared containing a compound which can complex molecular oxygen in a manner similar to that of the known biological oxygen-complexing proteins, myoglobin and hemoglobin, this solution is exposed to air or a similar oxygen-containing gas such that a large proportion of the oxygen-complexing compounds become complexed with oxygen. The solution is then removed from contact with the air and exposed to an environment induced by pressure or temperature changes in which the oxygen partial pressure is less than that in equilibrium with the oxygen-complexed compound, so that the compound gives up at least part of its oxgyen, thereby releasing into the environment a gas much richer in oxygen than that with which the solution was originally in contact.

One technique for separating oxygen from air involves the use of "immobilized liquid membranes". Such immobilized liquid membranes comprise a solid support, typically a synthetic polymer which is inert to oxygen, together with liquid immobilized within the inert support. The support may have very fine pores therein so that the liquid is contained therein by capillary forces, a polymer film acting as the support may be swollen by contact with the liquid to form a gel or various other techniques may be used for immobilizing the liquid within the support. Air or some other oxygen-containing gas is passed over one side of the immobilized liquid membrane, while the gas which passes through the membrane is removed by pumping on the opposite side of the membrane. The oxygen "diffuses selectively" through the liquid membrane, due to the presence of an oxygen partial pressure gradient between the two sides of the membrane. The oxygen molecules are carried in the form of a metal complex through the immobilized liquid membrane at a much greater net transport rate than the rate in which other gases are passed through the membrane. One such membrane system is disclosed in U.S. Pat. No. 3,396,510 which discloses a facilitated transport system using a liquid membrane and a non-volatile species which is soluble in the immobilized liquid which reversibly reacts with a specific gaseous component to be separated from the gaseous mixture. Although the patent discloses the possibility of facilitated transport of oxygen, the proposed system is primarily an aqueous-based one, utilizing water soluble complexing agents, and was found to be commercially unfeasible.

Daryle H. Busch, et al. in an article entitled "Molecular Species Containing Persistent Voids. Template Synthesis and Characterization of a Series of Lacunar-Nickel Complexes in the Corresponding Free Ligands", in J. Am. Chem. Soc. 103 pp 1472-1478 (1981), discloses a family of lacunar ligands synthesized in the form of nickel (II) complexes by a template process. The species disclosed were designed to provide a "lacuna" or protective void, or cavity, in the vicinity of a coordination site in order to facilitate the binding of small molecules to the metal ions. The species of complexes are characterized by having four N-atoms bound to a single nickel atom in a ligand system which results in an overall +2 charge for the complex.

Kuninobu Kasuga, et al. in an article entitled "A Preparation and Some Properties of Cobalt (II) Schiff-base Complexes and Their Molecular Oxygen Adducts", *Bull. Chem. Soc. Jpn.* 56, pp 95-98 (1983) disclose seven new cobalt (II) complexes with a tetradentate Schiff-base ligand and their three oxygen adducts. The disclosed complexes are reported to be stable at room temperature for several weeks and have the characteristic of having favorable affinity for molecular oxygen.

Roman, in U.S. Pat. Nos. 4,451,270 and 4,542,010 disclose processes and an apparatus for the separation and purification of oxygen and nitrogen. The processes utilize novel facilitated transport membranes to selectively transport oxygen from one gaseous stream to another, thereby leaving nitrogen as a by-product. In accordance with this process, an oxygen carrier capable of reversibly binding molecular oxygen is dissolved in a polar organic solvent and the resulting carrier solution is contained within a membrane which separates a gaseous feed stream, such as atmospheric air, to form a gaseous product stream. The oxygen carriers employed in the disclosed process are metal-containing complexes wherein a metal is bound by four ligating atoms, and has the capacity to reversibly bind oxygen and is also soluble in various polar organic solvents and reactive with axial bases.

U.S. Pat. No. 4,584,359 discloses a membrane of a vinyl polymer which contains oxygen-transferring groups not in solution, but in a chemically bonded form, which is used for separating molecular oxygen from a mixture of gases.

BRIEF SUMMARY OF THE INVENTION

The present invention is a class of pillared cobalt complexes which are capable of reversibly reacting with molecular oxygen. The cobalt complexes have the general structural formula:

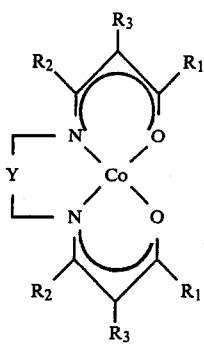

wherein each $R_1$ is independently, a phenyl or a $C_1$–$C_6$ alkyl group; each $R_2$ is independently hydrogen, a phenyl or a $C_1$–$C_6$ alkyl group; $R_3$ is either N-succinimido substituted with a $C_3$ or greater hydrocarbon functionality at the carbon atoms $\alpha$ to the imido carbonyl carbons, or a carbonyl functionality having a $C_1$ or greater hydrocarbon substituent with the proviso that if said substituent is methyl, $R_2$ cannot be hydrogen; and Y is o-phenylene, $-(CH_2)_a$ wherein "a" is 2 or 3, $-(CH_2)_b NR-(CH_2)_c$, wherein "b" and "c" are independently 1, 2 or 3 and $R_4$ is hydrogen or a $C_1$–$C_{12}$ alkyl group. The cobalt complexes described above have wide utility in oxygen separation operations. For example, the complex can be added to a solvent to form an oxygen adsorption medium, or can be present as an $O_2$ carrier in a gas-separation membrane.

DETAILED DESCRIPTION OF THE INVENTION

The present invention is a new class of cobalt complexes which are useful in oxygen separation processes. The new class of complexes differ from prior art complexes in that the structures of the new complexes enable them to achieve relatively long life and good $O_2$ affinity at near ambient temperatures.

The new class of cobalt complexes are pillared Schiff-base complexes having the general structural formula:

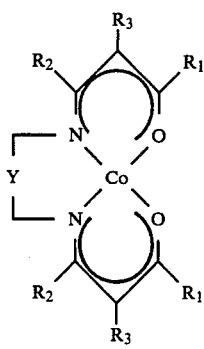

The structure is characterized by the presence of two keto-imine chelate ring moieties, joined by the linkage denoted by "Y" and having substituents $R_1$, $R_2$ and $R_3$. The substituent adjacent to each keto group, $R_1$, is independently, a phenyl or a $C_1$–$C_6$ alkyl group. The substituent adjacent to the imine group on each keto-imine moiety, $R_2$, is independently hydrogen, a phenyl or a $C_1$–$C_6$ alkyl group. "Y" may either merely serve to link the two keto-imine moieties, in which case Y is either o-phenylene or $-(CH_2)_a$ where "a" is 2 or 3; or Y may also contain a fifth ligating atom, in which case Y is $-(CH_2)_b NR_4-(CH_2)_c$, wherein "b" and "c" are independently 1, 2 or 3 and $R_4$ is hydrogen or a $C_1$–$C_{12}$ alkyl group.

Critical components of the present structure are the $R_3$ groups. Both $R_3$ groups are bulky groups which are generally oriented perpendicular to the plane of the Schiff-base ligand and provide a "pillaring" effect which protects against peroxo-bridged dimer formation. Consequently, the presence of bulky $R_3$ groups enhance the selectivity toward the formation of monomeric $O_2$ complexes. Each $R_3$ is either independently N-succinimido substituted with a $C_3$ or greater hydrocarbon functionality at the carbon atoms $\alpha$ to the imido carbonyl carbons, or $R_3$ is a carbonyl functionality having a $C_1$ or greater hydrocarbon substituent. The larger the $R_3$ group the greater the "pillaring" effect, however, for ease for synthesis and diffusion characteristics in membrane systems, it is often preferred that $R_3$ not be too large. Suitable examples of $R_3$ groups include carbonyl functionalities having the structural formula $COR_5$ wherein $R_5$ is phenyl, naphthyl, antharcyl, and fluorocarbon among others. Additionally, N-succinimido derivatives such as phthalimido are also well suited. While each $R_3$ group is independent of the other, for ease of synthesis, it is preferred that both $R_3$ groups of a single complex have the same structure.

The presence of the $R_1$ and $R_2$ groups serve to orient the $R_3$ group perpendicular to the plane of the ligand so as to achieve the "pillaring" effect. Consequently, it has been found that if $R_3$ is a smaller bulky group, i.e., a carbonyl functionality having a methyl substituent, $R_2$ must be $C_1$ or greater (i.e., $R_2$ cannot be hydrogen), to achieve sufficient pillaring effect to adequately prevent dimer formation.

All of the above described groups may have one or more suitable organic or inorganic substituents such as methyl, ethyl, halogens, etc. The above structure provides a small, neutrally charged complex which allows for good diffusion characteristics. Additionally, the presence of the election-withdrawing groups adjacent to the carbonyl carbons increases the resistance of the complexes to autoxidation. Further, the $R_3$ groups, militates against formation of bridged peroxy compounds which form irreversibly in previously known Schiff-base oxygen complexes.

The present cobalt complexes reversibly bond oxygen, and because of their favorable longevity and diffusion characteristics, are well suited for use in a wide variety of oxygen separation processes. Specifically, the complexes can be used in the presence of a solvent as a selective absorbent for oxygen to separate oxygen from other gaseous components; e.g., nitrogen, argon, etc. Alternatively, the complexes can be used as mobile $O_2$ carriers in gas-separation membranes. One specific embodiment comprises an immobilized liquid membrane containing the oxygen carrier as a mobile species.

An oxygen-containing gas mixture is brought into contact with the cobalt complex for a time sufficient for at least a portion of the oxygen to bind with the complex. The bound oxygen is subsequently released from the complex and recovered as product. The oxygen can be released by various means such as pressure differential, temperature differential, or any other suitable means. In cases in which the cobalt complexes are incorporated into membrane structures, the oxygen is transported across the membrane and subsequently released on the side opposite the feed.

In addition to the longevity and diffusion properties, the most fundamental property of the complex is oxygen affinity, as expressed by the equilibrium binding constant, $KO_2$, for the reaction:

$$LnCo + O_2 \underset{}{\overset{KO_2}{\rightleftarrows}} LnCo-O_2$$

wherein LnCo represents the cobalt complex.

Typically $KO_2$ is expressed as $K$ (torr$^{-1}$) which is calculated:

$$K = \frac{[LnCo-O_2]}{P_{O_2}[LnCo]} = \frac{1}{P_{\frac{1}{2}O_2}} \text{ (torr}^{-1})$$

The value for K therefore is the reciprocal of the pressure at which ½ of the available complex will be bound with oxygen at a given temperature.

The cobalt complexes of the present invention have good oxygen affinity e.g., K (torr$^{-1}$) between $10^{-1}$ and $10^{-3}$ at ambient temperature and pressure, and also exhibit good oxygen affinity at varying conditions.

The present oxygen complexes can be used as oxygen absorbents in any suitable solvent. Solvents found to be useful in the present invention are generally organic liquids or mixtures of organic liquids which are preferably polar, although non-polar liquids may be useful in some cases. In other cases, the solvent may comprise a mixture of organic liquids in water. The solvent must be able to dissolve a sufficient concentration; e.g., preferably in excess of 0.05M, of the complex. Classes of useful solvents include: lactones, lactams, sulfoxides, nitriles, amids, amines, esters, ethers and other nitrogen-containing liquids. In cases in which the cobalt complex in solution has a structure wherein "Y" does not contain a N-atom, an "axial-base" may have to be added to the solution if such a base is not a component of the solvent, itself. Such axial-bases provide an additional coordinating atom to those contained in the oxygen carrier, which assists in the reversible binding of the oxygen. Classes of axial bases found useful are imidazoles, ketones, amides, amines, sulfoxides, pyridines, etc.

Although the two most common applications for the present complexes are in membrane structures or in solution as absorbents, their stability makes them suitable for other possible applications, such as, components of solid state membranes, or for use in "air" batteries where gaseous $O_2$ forms part of one electrode.

Synthesis of the cobalt complex is typically carried out by preparing a precursor nickel or copper compound wherein the nickel or copper is bound to two oxygen and two nitrogen atoms. The precursor compound then undergoes demetallation to remove the nickel or copper and form a free ligand. The free ligand is subsequently reacted with a source of cobalt to form the cobalt complex. The examples below illustrate specific techniques for synthesizing various pillared cobalt complexes and the use of these complexes in binding oxygen. These examples are only illustrative and are not meant to limit the scope of the present invention.

EXAMPLES

Various pillared cobalt complexes as described above were synthesized. All the experiments were carried out under moisture-free conditions. Initially three different precursor complexes (I, II and III) were prepared having the structural formula:

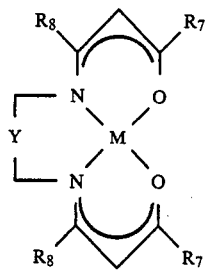

wherein
(I) $R_7=CH_3$; $R_8=H$; $Y=-(CH_2)_2$; M=Ni
(II) $R_7=R_8=CH_3$; $Y=-(CH_2)_2$; M=Cu or Ni
(III) $R_7=R_8=CH_3$; $Y=(CH_2)_3$

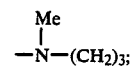

M=Cu. The precursors were formed by known literature routes, such as taught by L. Wolf, et al. *Anorg. Allg. Chem.*, 1966, 346, 76; Y. Chen, et al. *Inorg. Chem.*, 20, 1885 (1981) and P. J. McCarthy, et al. *J. Am. Chem. Soc.* 1955, 77, 5820.

The acid chloride, m-anisoyl chloride, was obtained from Aldrich Chemical Company. Benzene and triethylamine were dried over $CaH_2$ and then distilled.

EXAMPLE 1

Synthesis of a pillared cobalt complex wherein:

$R_1 = R_2 = CH_3$; $Y = -(CH_2)_2$;

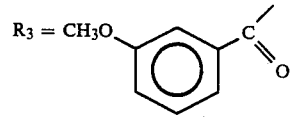

(a) 1.90 gm (6.77 mmole) of the precursor complex, (II), M=Ni was dissolved in 200 ml of dry benzene. To this, 1.37 gm (13.54 mmole) of triethylamine was added, followed by 2.30 gm (13.54 mmole) of m-anisoyl chloride. The mixture was refluxed for three days with stirring. The triethylamine hydrochloride was filtered and the solvent was removed on a rotary evaporator. The contents of the flask were dissolved in a minimum volume of chloroform and chromatographed on an alumina column. A fast moving orange-red band was collected by eluting with chloroform. Addition of ethanol, followed by reduction in the volume of the solvent, resulted in the precipitation of the pillared nickel complex. Yield: 2.80 gm (5.10 mmoles, 75%).

One gram (1.82 mmole) of the pillared nickel complex was reacted with 0.8 gm of p-toluene sulfonic acid in acetonitrile with gentle warming. The color of the solution immediately became green. After removal of all the solvent by rotary evaporation, water was added to precipitate an oily yellow solid. Chloroform was added to dissolve the solid and the solution was dried with anhydrous sodium sulfate. Reduction of the volume of the solvent followed by the addition of diethyl ether resulted in the formation of a pale yellow solid. The $^{13}C$ nmr of this solid was identical to that of the free ligand obtained by the demetallation of the pillared copper complex. Yield: 0.60 gm (1.21 mmole, 66%).

(b) The pillared cobalt complex was prepared by the following procedure. 0.40 gm (0.80 mmole) of the free ligand was reacted with 0.24 gm (0.96 mmole) of cobalt acetate monohydrate and 0.077 gm (1.92 mmole) of sodium hydroxide in methanol. Gentle reflux for a few hours yielded an orange solution and a bright yellow precipitate. The yellow precipitate was filtered and recrystallized from methylene chloride and methanol to get ≈200 mg of product. The filtrate, on long standing, gave another 100 mg of product. Overall yield: 0.30 gm (68%). Infrared: C=O (1650 cm$^{-1}$) strong.

EXAMPLE 2

Synthesis of a pillared cobalt complex wherein:

$R_1 = CH_3$; $R_2 = H$; $Y = (CH_2)_7$;

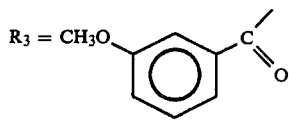

$R_3 = CH_3O$ (a) 0.73 gm (2.89 mmoles) of the precursor complex, (II), M=Ni was dissolved in 125 ml of dry benzene. To this, 0.82 ml of triethylamine was added, followed by 0.82 ml of m-anisoyl chloride. After refluxing for 60 hours, the solution was filtered to remove triethylamine hydrochloride, and rotovaped to dryness. The contents of the flask were dissolved in a minimum volume of chloroform and chromatographed on an alumina column. A fast moving orange-red band was eluted with chloroform. Ethanol was added to the solution and the volume was reduced on a rotary evaporator. This resulted in the precipitation of the orange-red product. Yield: 1 gm (1.91 mmole, 65%).

(b) The desired pillared cobalt complex was synthesized from the resultant nickel complex in accordance with the procedures set out in step (b) of Example 1 above.

EXAMPLE 3

Synthesis of a pillared cobalt complex wherein:

$$R_1 = R_2 = CH_3; Y = (CH_2)_3-\overset{CH_3}{\underset{|}{N}}-(CH_2)_3;$$

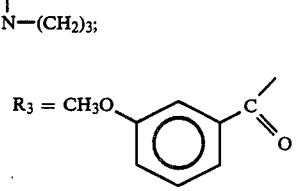

$R_3 = CH_3O$ (a) 1.298 gm (3.5 mmole) of the precursor complex, (III), M=CU was dissolved in 120 ml of dry benzene containing 1 ml of triethylamine. 1.194 gm (7.0 mmole) of m-anisoyl chloride was dissolved in benzene and added over a period of 40 minutes. The solution was stirred a room temperature over a period of 48 hours. The white precipitate of triethylamine hydrochloride was filtered. The benzene was removed on a rotary evaporator and the resulting oil was dissolved in petroleum ether. Upon cooling, the pillared copper complex was obtained as a green powder in 98% yield.

The complex (1.2 gm) was dissolved in 100 ml of dry chloroform. Hydrogen sulfide was bubbled for ten minutes and the copper sulfide precipitate was filtered over celite. The solvent was removed under vacuo to get a yellow oil that was identified as the pillared free ligand by $^{13}C$ nmr.

(b) 0.3532 g (0.61 mmole) of the ligand synthesized in step (a) was suspended in ≈50 ml of dry t-butyl alcohol. To this, 0.389 gm (0.61 mmole) of $(Et_4N)_2CoBr_4$ was added, followed by 0.137 gm (1.2 mmole) of potassium t-butoxide; at this point the solution turned red-brown. The solution was stirred for 2½ hours and the solvent was removed under vacuo, 200 ml of dry benzene was added, stirred for two hours and then filtered. The solvent was removed and the products recrystallized from $CH_2Cl_2$/pet ether to get a dark yellow powder. Yield: 65%; IR, 1630 cm$^{-1}$ (C=O) strong.

EXAMPLE 4

To demonstrate the utility of the present pillared cobalt complexes for binding oxygen, the complex synthesized in Example 1 above was dissolved in a solution containing 2% pyridine in toluene. The solution was contacted with a gas stream containing nitrogen and oxygen at −15° C. The binding constants ($KO_2$) with oxygen for the complex were calculated, and the results are reported below.

| Wavelength* (nm) | $KO_2$ (torr$^{-1}$) | Standard Deviation |
|---|---|---|
| 370 | 2.574 | 0.433 |
| 360 | 2.865 | 0.424 |
| 350 | 3.031 | 0.432 |
| 342 | 3.160 | 0.447 |

*Wavelength of light used to measure the concentration of oxygenated and unoxygenated complex.
A $KO_2$ of 3.0 (torr$^{-1}$) = $P_{1/2}(O)$ = $1/3.0$ = 0.33 torr The above results indicate that at −15° C., ½ of the complex will be bound with oxygen at a pressure of only 0.33 torr. Increasing the pressure will result in more oxygen being bound while decreasing the pressure will cause the oxygen to be released.

EXAMPLE 5

The pillared cobalt complex synthesized in Example 3 was dissolved in toluene, and the resulting solution was contacted with a gas stream containing nitrogen and oxygen at −20° C. The binding constants ($KO_2$) with oxygen for the complex were calculated, and the results are reported below.

| Wavelength (nm) | $KO_2$ (torr$^{-1}$) |
|---|---|
| 350 | 12.4 ± 0.8 |
| 360 | 12.6 ± 0.8 |
| 370 | 13.0 ± 0.9 |
| 380 | 12.8 ± 0.9 |
| 400 | 12.6 ± 0.9 |

The above results indicate that at low temperatures, the complexes have a high affinity for oxygen even at low pressure.

EXAMPLE 6

Pillared cobalt complexes wherein $R_3$ is a substituted N-succinimido were synthesized by initially synthesizing a precursor compound having the structural formula

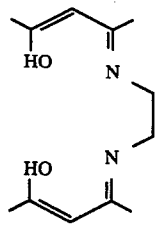

by standard routes as described by P. J. McCarthy, et al. *J. Am. Chem. Soc.*, 1955, 77, 5820.

(a) SYNTHESIS OF Br$_2$ ACACEN 10 g of the above precursor compound was dissolved in 50 ml CHCl$_3$, 10 mg of benzoyl peroxide added, then 15.9 g of powdered N-bromosuccinimide added directly over 5 mins. A mild exotherm was observed and the solution became progressively cloudier. Stirring was continued at room temperature for 45 minutes followed by filtration which yielded a white solid. This was boiled in 800 ml. MeOH, concentrated by boiling to 400 ml then left to cool and crystallize. Filtration of first cooling yielded 8.0 g pure Br$_2$acacen. Reconcentration and cooling of liquors yielded a further 1.4 g. Total yield=9.4 g.

(b) SYNTHESIS OF A PILLARED COBALT COMPLEX wherein: R$_1$=R$_2$=CH$_3$; Y=(CH$_2$)$_2$; R$_3$=phthalimido functionality 0.485 g of potassium phthalimide and 0.5 g Br$_2$acacen were loaded into a 100 ml three-necked round bottom flask fitted with a condenser. Under a blanket of nitrogen, 50 ml dry DMF was added and the mixture refluxed for 30 minutes. After cooling, a small amount of white solid was filtered off, the filtrate added to 500 ml H$_2$O and this mixture extracted with 3×10 ml dichloromethane. The organic layer was then washed ×3 with H$_2$O and dried over anhydrous Na$_2$SO$_4$. Evaporation yielded a yellow oil, plus some crystals which were filtered and recrystallized from 50/50 dichloromethane/methanol. Yield: 0.35 pure (phth)$_2$acacen ligand (52% of theoretical).

Under a blanket of nitrogen, 0.20 g (phth)$_2$acacen was treated with 36 mg of sodium metal predigested in 5 ml methanol. To this was added 86 mg CoBr$_2$ in 5 ml MeOH and the mixture refluxed for 30 minutes. An initial yellow color was observed followed by the formation of an orange powder which was filtered off as the desired pillared cobalt complex.

(c) USE OF THE COMPLEX TO BIND OXYGEN

A solution of the above synthesized complex in either toluene +5% N-methyl imadazole or 1,2 dichloro ethane +5% pyridine was observed to reversibly bind O$_2$ at room temperature. Exposure to air caused a rapid darkening in color. Application of vacuum or flushing with nitrogen restored the original color.

EXAMPLE 7

SYNTHESIS OF A PILLARED COBALT COMPLEX WHEREIN:

R$_1$ = R$_2$ = CH$_3$; Y = (CH$_2$)$_2$;

-continued
R$_3$ =

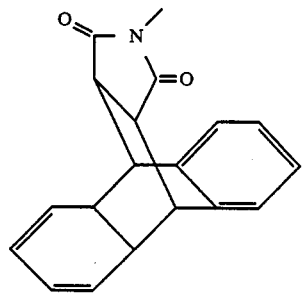

0.25 g of the Diels Alder adduct of maleimide and anthracene, prepared as taught by Ray, et al, *JACS*, 74, 1247 (1952) was mixed with 50 mg KOH in 10 ml absolute ethanol and boiled for 10 minutes. This produced a white precipitate which was filtered, dried, then added to 10 ml DMF. 174 mg Br$_2$acacen and excess K$_2$CO$_3$ were added and this mixture stirred 18 hours at room temperature. 500 ml H$_2$O were then added and the resultant suspension extracted ×3 with 50 ml CHCl$_3$. The organic layer was washed with H$_2$O and dried over anhydrous Na$_2$SO$_4$. Evaporation gave a yellow oil which was boiled in a minimum of 50:50 methanol/dichloromethane to give a crystalline white material ($\approx$20 mg). $^1$HNMR spectroscopy indicated this to be substantially the free ligand of the desired cobalt complex.

Under a blanket of nitrogen, this free ligand was dissolved in 100 ml MeOH/toluene 50:50 and shaken vigorously with excess CoBr$_2$+KOH for 10 minutes. The organic layer was washed with H$_2$O to give a turbid orange solution. Drying over anhydrous NaSO$_4$ overnight gave a transparent orange solution. Evaporation gave a yellowish solid. Addition of acetonitrile broke this up into a slurry of orange microcrystals of the Cobalt Complex having the above structure.

Diacetamide or acetonitrile solutions of the above cobalt complex in the presence of a trace of pyridine, were observed to reversibly bind oxygen.

Since maleimide is an excellent dienophile in Diels Alder reactions, it is capable of reacting with a wide range of diene-containing substances. The preparation of the above cobalt complex demonstrates that such Diels Alder adducts could be reacted with Br$_2$acacen to give a whole new series of pillared complexes.

Having thus described the present invention, what is now deemed appropriate for Letters Patent is set out in the following appended claims.

What is claimed is:

1. A method for separating oxygen from a gaseous mixture comprising oxygen and at least one other component, said method comprising: bringing said gaseous mixture into contact with a cobalt complex having the structural formula:

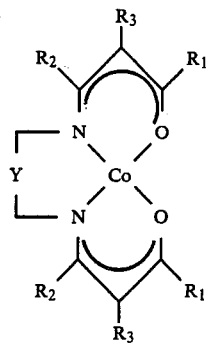

wherein each $R_1$ is independently, a phenyl or a $C_1$-$C_6$ alkyl group; each $R_2$ is independently hydrogen, a phenyl, or a $C_1$-$C_6$ alkyl group; $R_3$ is either N-succinimido substituted with a $C_3$ or greater hydrocarbon functionality at the carbon aoms α to the imido carbonyl carbons, or a carbonyl functionality having a $C_1$ or greater hydrocarbon substituent with the proviso that if said substituent is metyl, $R_2$ cannot be hydrogen; and Y is o-phenylene, $-(CH_2)_a$ wherein "a" is 2 or B 3, $-(CH_2)_b NR_4(CH_2)_c$ wherein "b" and "c" are independently 1, 2 or 3 and $R_4$ is hydrogen or a $C_1$-$C_{12}$ alkyl group, such that at least a portion of the oxygen present in the gaseous mixture is reversibly bound to said cobalt complex.

2. A method in accordance with claim 1 wherein said bound oxygen is subsequently released from said cobalt complex and recovered as product.

3. A method in accordance with claim 1 wherein said cobalt complex is present as an $O_2$ carrier in a gas-separation membrane.

4. A method in accordance with claim 3 wherein said membrane comprises a liquid medium containing the cobalt complex as a mobile species.

5. A method in accordance with claim 1 wherein said cobalt complex is present in an absorbent solution.

6. A method in accordance with claim 5 wherein said absorbent solution also contains an axial base.

7. A method in accordance with claim 1 wherein said gaseous mixture is brought into contact with the cobalt complex at about ambient temperature.

8. A method in accordance with claim 7 wherein said oxygen-containing gaseous mixture also contains nitrogen and argon.

9. A method in accordance with claim 1 wherein said cobalt complex has a structure wherein $R_3$ is a carbonyl functionality having the structural formula $COR_5$ wherein $R_5$ is phenyl, naphthyl, antharcyl or fluoronyl.

10. A method in accordance with claim 1 wherein each $R_1$ is $CH_3$, each $R_2$ is $CH_3$ and Y is $-CH_2)_2$.

11. A method for separating oxygen from a gaseous mixture comprising oxygen and at least one other component, said method comprising:

bringing said gaseous mixture into contact with a cobalt complex having the structural formula:

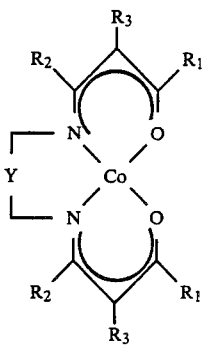

wherein each $R_1$ is independently, a phenyl or a $C_1$-$C_6$ alkyl group; each $R_2$ is independently hydrogen, a phenyl, or a $C_1$-$C_6$ alkyl group; $R_3$ is either a phthalimido group or $CH_3OC_6H_4CO$; and Y is o-phenylene, $-(CH_2)_a$ wherein "a" is 2 or 3, or $-(CH_2)_b NR_4(CH_2)_c$ wherein "b" and "c" are independently 1, 2 or 3 and $R_4$ is hydrogen or a $C_1$-$C_{12}$ alkyl group, such that at least a portion of the oxygen present in the gaseous mixture is reversibly bound to said cobalt complex.

12. A cobalt complex having the structural formula:

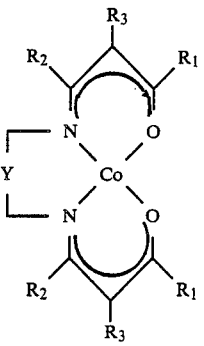

wherein each $R_1$ is independently, a phenyl or a $C_1$-$C_6$ alkyl group; each $R_2$ is independently hydrogen, a phenyl, or a $C_1$-$C_6$ alkyl group; $R_3$ is either N-succinimido substituted with a $C_3$ or greater hydrocarbon functionality at the carbon atoms α to the imido carbonyl carbons, or a carbonyl functionality having a $C_1$ or greater hydrocarbon substituent with the proviso that if said substituent is methyl, $R_2$ cannot be hydrogen; and Y is o-phenylene, $-(CH_2)_a$ wherein "a" is 2 or 3, $-(CH_2)_b NR_4(CH_2)_c$, wherein "b" and "c" are independently 2 or 3 and $R_4$ is hydrogen or a $C_1$-$C_{12}$ alkyl group.

13. A cobalt complex in accordance with claim 12 wherein $R_3$ is a carbonyl functionality having the structural formula $COR_5$ wherein $R_5$ is phenyl, naphthyl, anthracyl or fluorocarbon.

14. A cobalt complex in accordance with claim 12 wherein Y is $-CH_2)_2$.

15. A cobalt complex in accordance with claim 12 wherein each $R_1$ is $CH_3$ and each $R_2$ is $CH_3$.

16. A cobalt complex in accordance with claim 12 wherein each $R_1$ is $CH_3$, each $R_2$ is H, and Y is $-(CH_2)_2$.

17. A cobalt complex in accordance with claim 12 wherein said complex is neutral in charge.

18. A cobalt complex in accordance with claim 12 wherein said complex has the capacity to selectively and reversibly bind oxygen.

19. A cobalt complex having the structural formula:

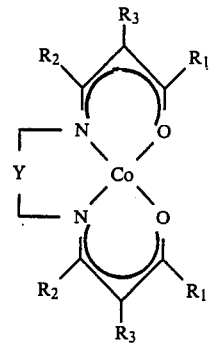

wherein each $R_1$ is independently, a phenyl or a $C_1$–$C_6$ alkyl group; each $R_2$ is independently hydrogen, a phenyl, or a $C_1$–$C_6$ alkyl group; $R_3$ is either a phthalimido group or $CH_3OC_6H_4CO$; and Y is o-phenylene, $-(CH_2)_a-$ wherein "a" is 2 or 3, or $-(CH_2)_b NR_4(CH_2)_c-$ wherein "b" and "c" are independently 2 or 3 and $R_4$ is hydrogen or a $C_1$–$C_{12}$ alkyl group.

20. A cobalt complex in accordance with claim 19 wherein $R_3$ is $CH_3OC_6H_4CO$ with the ether linkage in the meta position.

* * * * *